United States Patent [19]
Shen

[11] Patent Number: 5,794,295
[45] Date of Patent: Aug. 18, 1998

[54] ELECTRICALLY OPERATED OSCILLATORY TOOTHBRUSH

[76] Inventor: Chung-Shan Shen, Suite 2, 7F, No. 95-8 Chang Ping Road, Sec. 1, Taichung, Taiwan

[21] Appl. No.: 613,321

[22] Filed: Mar. 11, 1996

[51] Int. Cl.$^6$ .................................................. A46B 13/02
[52] U.S. Cl. ................................... 15/22.1; 15/22.4
[58] Field of Search ......................... 15/22.1, 22.4, 15/23, 24, 28, 29

[56] References Cited

U.S. PATENT DOCUMENTS

| | | | |
|---|---|---|---|
| 1,869,991 | 8/1932 | White | 15/22.4 |
| 3,800,350 | 4/1974 | Francolino | 15/23 |
| 4,397,055 | 8/1983 | Cuchiara | 15/23 |
| 5,381,576 | 1/1995 | Hwang | 15/22.1 |
| 5,442,827 | 8/1995 | Hommann | 15/22.1 |
| 5,465,444 | 11/1995 | Bigler | 15/22.1 |
| 5,504,959 | 4/1996 | Yukawa | 15/22.4 |
| 5,504,960 | 4/1996 | Hommann | 15/22.1 |

FOREIGN PATENT DOCUMENTS

| | | | |
|---|---|---|---|
| 0626651 | 1/1963 | Belgium | 15/22.1 |
| 0021654 | 2/1978 | Japan | 15/22.1 |

*Primary Examiner*—Randall Chin

[57] ABSTRACT

An electrically operated oscillatory toothbrush comprises generally a housing, a motor in the housing, an actuator, an oscillator and a sleeve member sequentially secured to the top of the housing and protected by a cap member, and a toothbrush secured into the upper portion of the cap member. The character of this disclosure is that the sleeve member has a transverse slot in cooperation with a recoil spring connected between the oscillator and the sleeve member so as to limit the oscillator to swing within a certain range of angle in order that the toothbrush oscillates with intermittent elastic vibrations to an extent to perfectly clean a user's teeth.

2 Claims, 9 Drawing Sheets

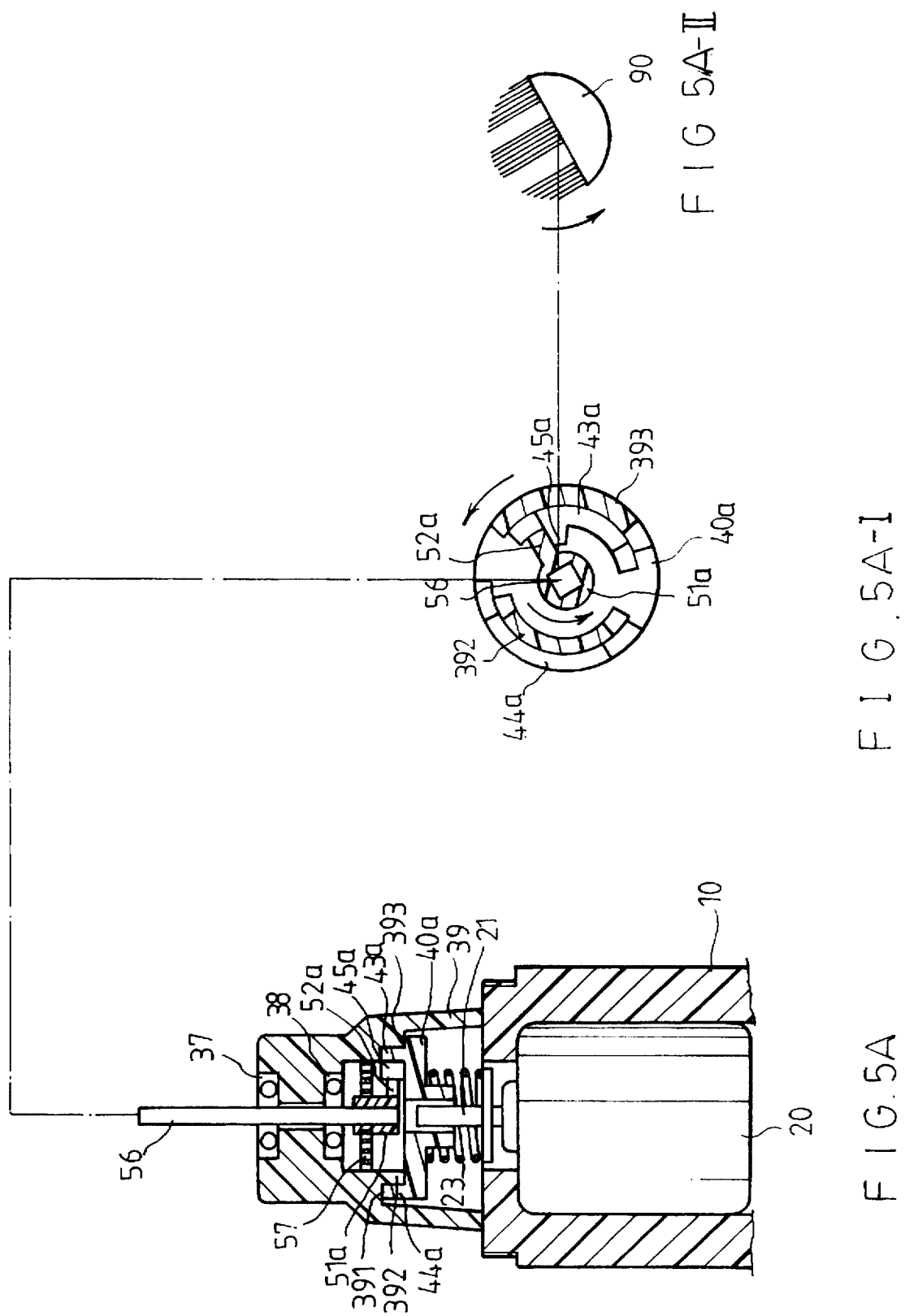

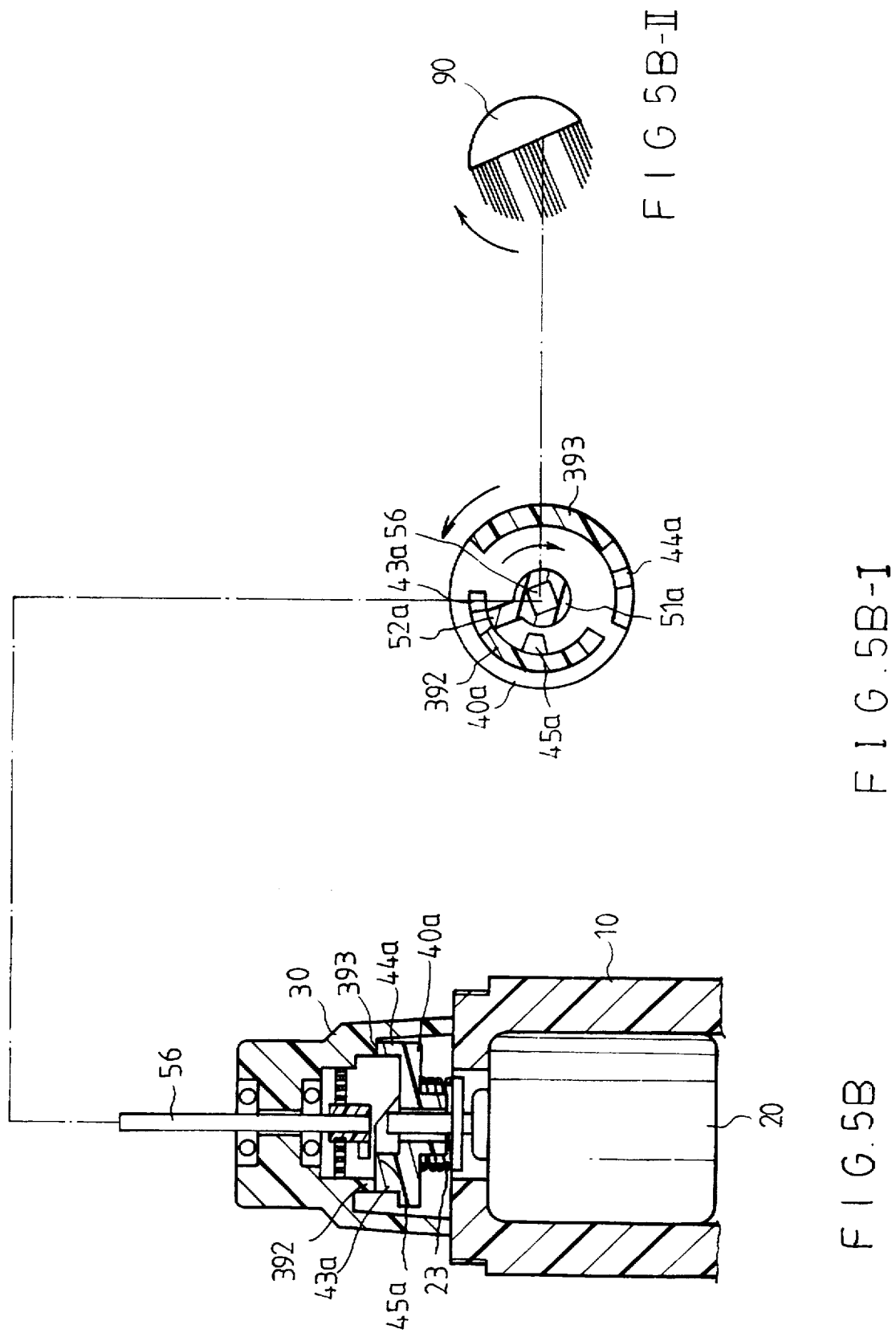

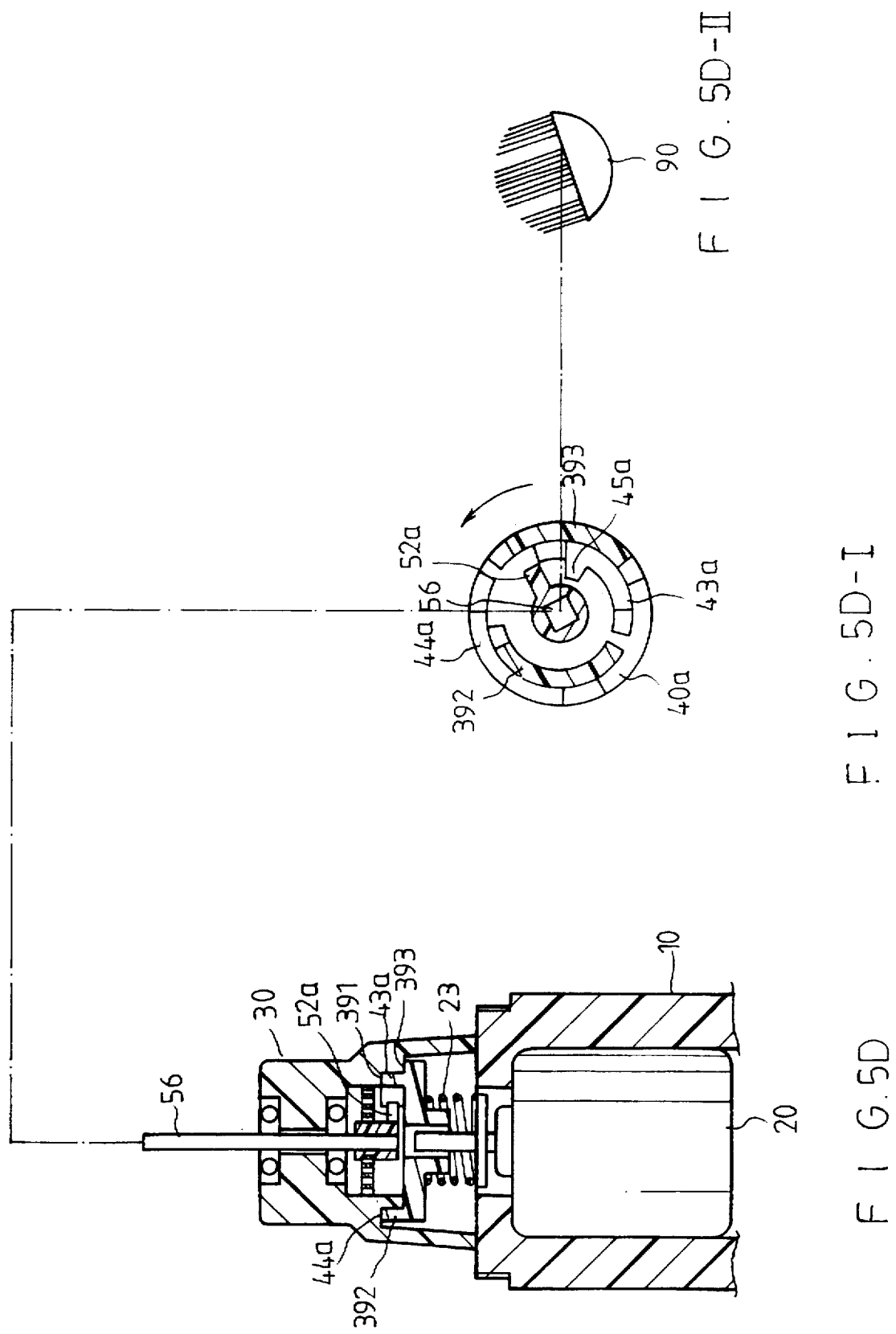

ELECTRICALLY OPERATED OSCILLATORY TOOTHBRUSH

BACKGROUND OF THE INVENTION

The present invention relates to automatic tooth brushes, and more particularly to an electrically operated oscillatory toothbrush which provides intermittent elastic vibration along with it's oscillatory movements.

Improper application of a toothbrush cannot throughly clean up the tartar on the teeth but wears the gums out of the teeth causing dispensable damagement. To timely and properly brush the teeth is the only way to maintain the sanitation for the cavity of the mouth. According to the latest dentist research report, the best way to brush the teeth is to apply the toothbrush following the veins of the teeth with the bristle of the toothbrush perpendicular to the surface of the teeth. As for an automatic toothbrush, a better cleaning effect will be achieved if an elastic vibration is intermittently occurred in accompanying with the oscillatory movements of the toothbrush.

SUMMARY OF THE PRESENT INVENTION

The present invention has a main object to provide an electrically operated oscillatory toothbrush which is structurally improved to include intermittent elastic vibrations in accompanying with the oscillatory movements of the toothbrush.

Accordingly, the electrically operated oscillatory toothbrush of the present invention is generally comprised of a housing, a motor disposed therein to drive an actuator which in turn drives an oscillator to effect the toothbrush performing repeated oscillatory movements within a certain range of angle. An intermittent elastic vibration accompanies with each of the oscillatory movement so as to ensure a perfect cleaning effect for the users to brush their teeth.

The present invention will become more fully understood by reference to the following detailed description thereof when read in conjunction with the attached drawings.

DETAILED DESCRIPTION OF THE PREFERRED EMBODIMENT

Figure 1:
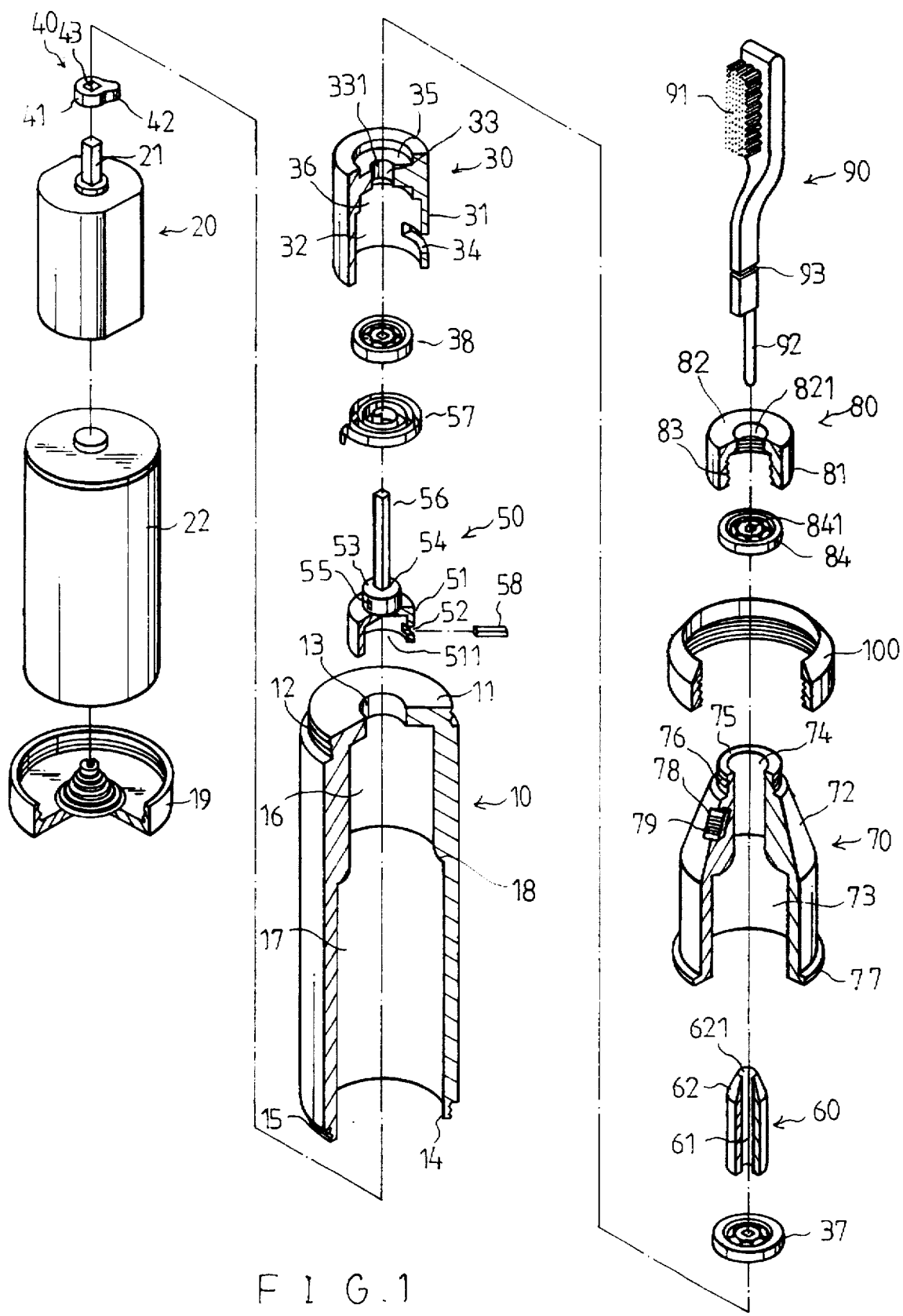
FIG. 1 is an exploded perspective view to show a preferred embodiment of the present invention.
Figure 2:
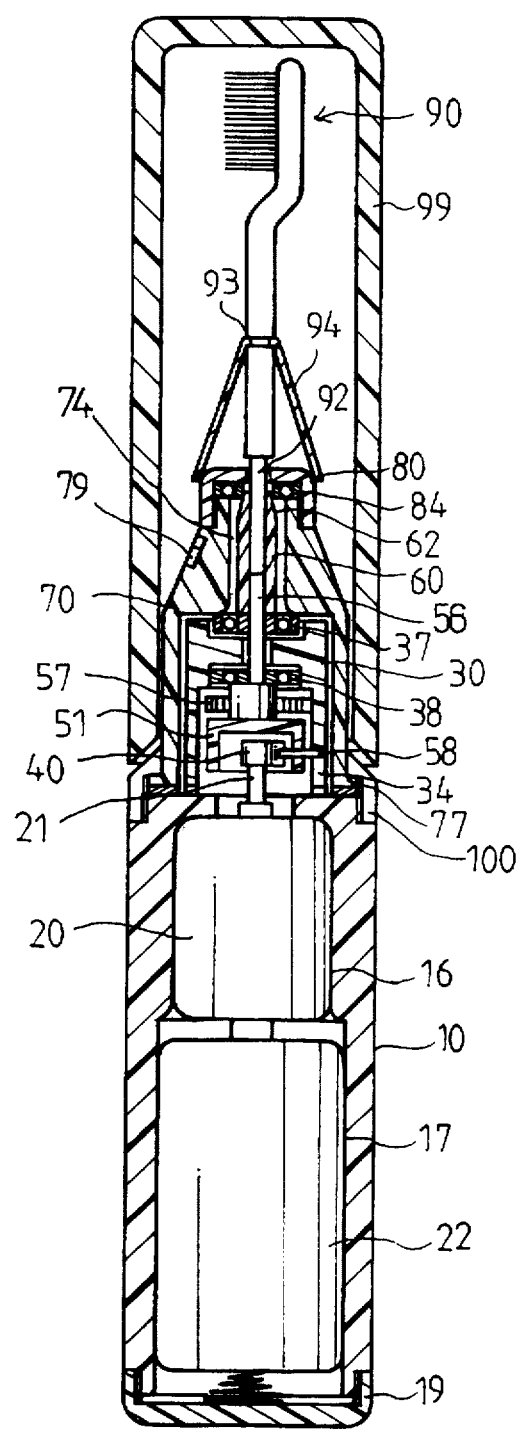
FIG. 2 is a sectional view to show an assembled oscillatory toothbrush of FIG. 1, FIGS. 3A to 3D' are the sectional views to schematically illustrate the operations of the preferred embodiment of the present invention.

With reference to FIGS. 1 and 2 of the drawings, the electrically operated oscillatory toothbrush of the present invention comprises generally a tubular housing 10, an electrical motor 20, a sleeve member 30, an actuator 40, an oscillator 50, a chuck member 60, a cap member 70, a fastener 80 and a toothbrush 90.

The tubular housing 10 has a less diameter bottom 11 including peripheral thread 12 and a first axial hole 13 at center thereof, a less diameter neck 14 at lower end including also peripheral thread 15 therearound, a first chamber 16 and a large diameter second chamber 17 defining a shoulder 18 thereinbetween.

The electrical motor 20 is fixedly secured into the first chamber 16 having a rectangular shaft 21 eccentrically protruded outward from the axial hole 13 and exposed above the bottom 11. A battery 22 disposed into the second chamber 17 and secured by a cover 19 which fastens onto the neck 14 (as shown in FIG. 2). The motor 20 is actuated by the battery 22.

The actuator 40 has an annular body 41, a push means 42 extended outward from a periphery and a rectangular central bore 43 having a size equal to the outer configuration of the shaft 21 so as to fixedly wrap thereon.

The oscillator 50 has an annular body 51 defining a receiving space 511 therein, a peripheral aperture 52, a less diameter member 53 having a rectangular axial hole 54 in the top and a vertical slot 55 in a periphery for respectively securing a rectangular axle rod 56 and one end of a recoil spring 57 therein and allowing the spring 57 wrapped onto the outer periphery of the less diameter member 53, and pawl 58 inserted into the aperture 52. The oscillator 50 is axially disposed onto the top of the housing 10 with the actuator 40 received into the receiving space 511 and the push means 42 thereof engaged with the pawl 58.

The sleeve member 30 has a hollow cylinder body 31 defining a third chamber 32 therein, a bottom 33 at the upper end including a second axial hole 331 at the center and a transverse slot 34 of predetermined length in a peripheral wall. Further, first and a second circular cavities 35 and 36 are formed on the opposite side of the bottom 33 for respectively receiving first and a second bearings 37 and 38 therein. The bearings 37 and 38 each have a rectangular central bore 371 and 381 sizeably equal to the body of the axle rod 56 so as to allow the axle rod 56 to be inserted therethrough when the sleeve member 30 axially covers the oscillator 50. The other end of the recoil spring 57 secures to an inner wall of the third chamber 32 and the other end of the pawl 58 is received in the transverse slot 34 and normally stops against one end, namely the right side of the slot 34.

The chuck member 60 has a cylinder body, a rectangular central bore 61, a tapered end 62 on the top thereof. The tapered end 62 has a plurality of vertical slots 621 spaced apart so as to provide certain flexibility to the tapered end 62 for centripetally gripping the toothbrush 90 when it inserts in. The chuck member 60 is sleeved onto the axle rod 56 above the first bearing 37.

The cap member 70 has a cylinder body 71 abutting a tapered upper portion 72, a hollow interior defining a fourth chamber 73 for receiving the sleeve member 30 therein, a central bore 74 for allowing the chuck member 60 to pass through, a neck 75 on the top thereof having threaded outer periphery 76, a flange 77 extended outward from the lower rim thereof, and a recess 78 on a peripheral wall of the tapered upper portion 72 for securing a switch 79 which is a conventional waterproof type including a button and wires necessary to transmit electric power between the battery 22 and the motor 20 (not shown). The flange 77 of the cap member 70 has an outer diameter equal to that of the bottom 11 of the housing 10. When the cap member 70 covers on the sleeve member 30, the flange 77 thereof will exactly engage within the circumference of the bottom 11 to facilitate the cap member 70 axially connected with the housing 10 by means of a locking ring 100. After the connection of the cap member 70 with the housing 10, the upper portion of the chuck member 60 is exposed to the outside of the cap member 70.

The fastener 80 has an annular body 81, an axle hole 821 centrally formed in an upper bottom 82 for passing the toothbrush therethrough and a threaded inner periphery 83 made in registry with the threaded outer periphery 76 of the neck 75. A third bearing 84 has a tapered central hole 841 made in registry with the tapered end 62 of the chuck member 60 so as to engage with each other. The fastener 80 is axially screwed onto the neck 75 of the cap member 70 with the upper surface of the third bearing 84 against the inner surface of the bottom 82.

The toothbrush 90 has a conventional bristle head 91 and a connection rod 92 which inserts into the tapered end 63 of the chuck member 60 and tightened by the fastener 80 in the manner such that to rotate the fastener 80 clockwise will press the third bearing 84 moving inward to force the tapered end 62 to move centripetally so as to tightly grip the connection rod 92 of the toothbrush 90, and an annular groove 93 on the shank for securing a waterproof device 94 which is made from flexible material, has a conical body, a minimum diameter equal to the diameter of the groove 93 and a maximum diameter equal to the outer diameter of the fastener 80. This is so that the device 94 can be secured to the groove 93 and the fastener 80 therebetween (as shown in FIG. 2) and can be twisted to cope with the oscillatory movement of the toothbrush 90.

Finally a tubular cover 99 is provided to protect the toothbrush when it is not in use.

Figure 3A:
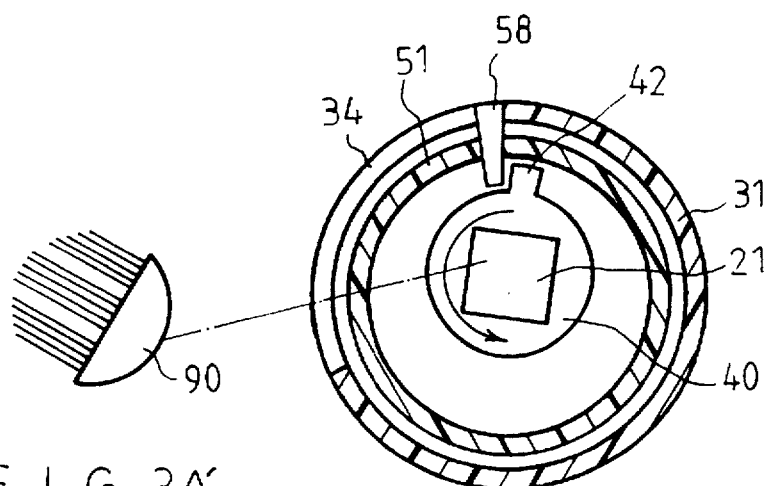
Figure 3B:
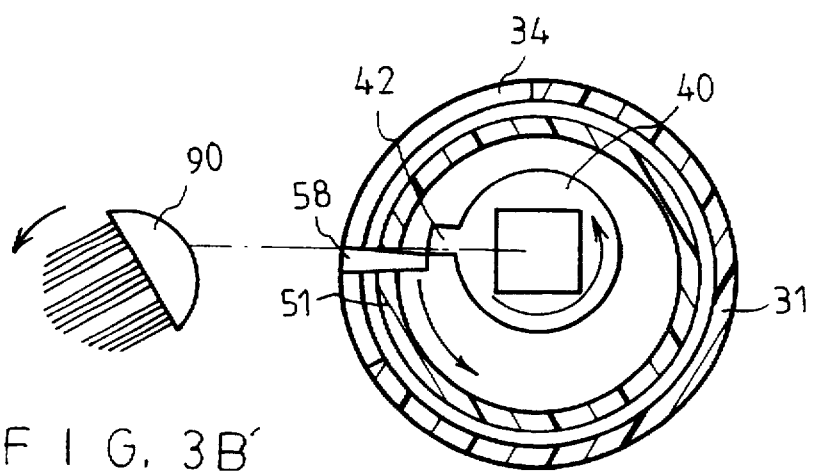
Figure 3C:
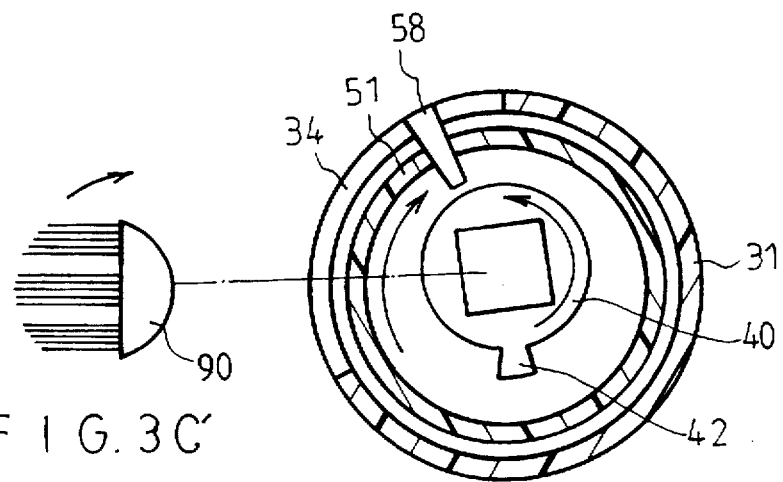
Figure 3D:
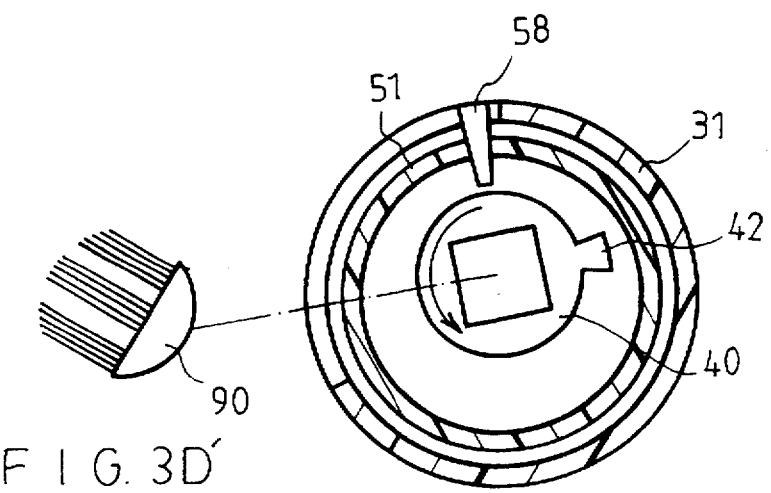
Figure 4:
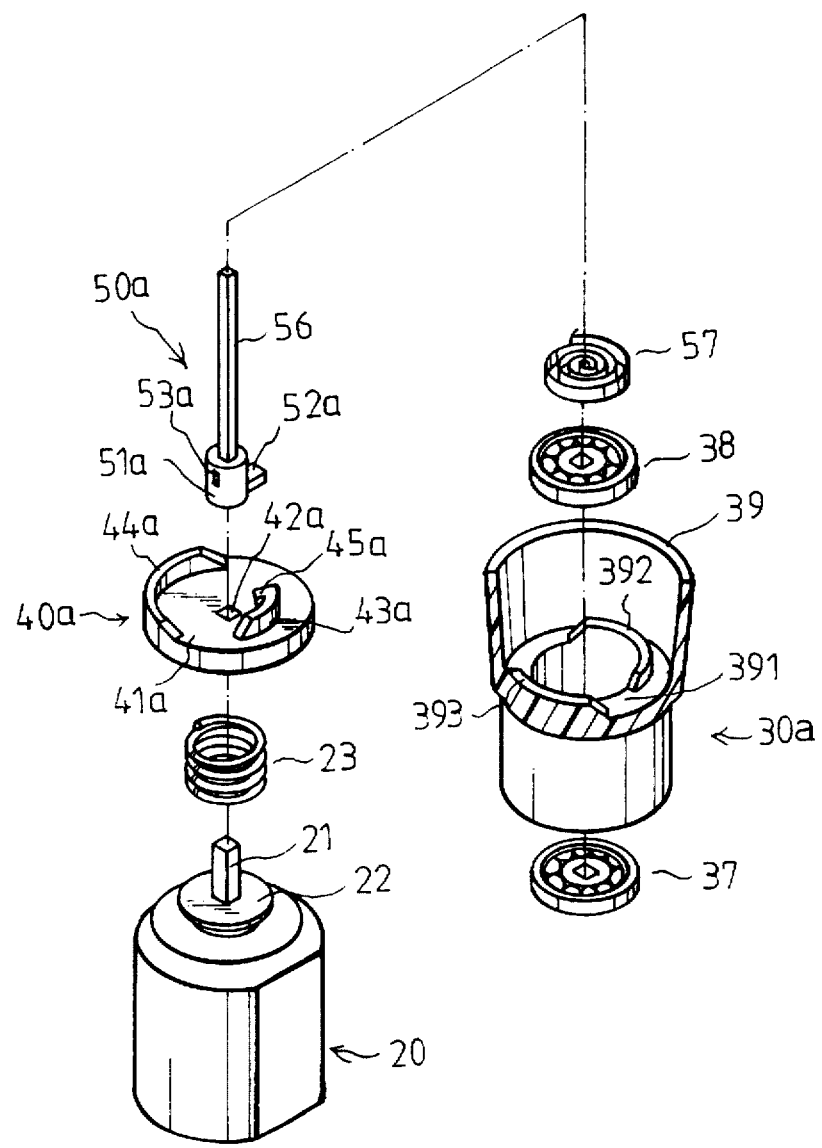
FIG. 4 is an exploded perspective view to show an alternative embodiment of the present invention, and FIGS. 5A to 5D-II are the sectional views to schematically illustrate the operations of the alternative embodiment of the present invention.

Referring to FIGS. 3A to 3D', the pawl 58 under the recoiling force of the spring 57 normally stops against one end, namely the right side of the slot 34 (as shown in FIG. 3A). In operation, when the switch is on, the actuator 40 will be driven by the motor 20 to constantly rotate counterclockwise and in turn the push means 42 thereof pushes the pawl 58 moving toward the other end, namely the left side of the slot 34 (as shown in FIG. 3B). The push means 42 of the actuator 40 departs from the pawl 58 when it reaches to the left side of the slot 34 because of the eccentricity of the shaft 21 and the pawl 58 is recoiled by the spring 57 from the left side back to the right side of the slot 34 and makes a bumping hereto (as shown in FIGS. 3C and 3D). When the push means 42 returns to push the pawl 58 again, it acts as recited above so that the continuous rotation of the actuator 40 makes the pawl 58 perform repeated oscillatory and bumping movements within the slot 34. Because of that, the oscillator 50 acts synchronously with the pawl 58, it indirectly drives the toothbrush to perform repeated oscillatory actions within a certain range of angle together with the intermittent elastic vibrations.

Referring to FIGS. 4 and 5A to 5D-II, an alternative embodiment of the present invention is shown. In this embodiment, the general function and structure of the oscillatory toothbrush is mostly similar to that illustrated in FIGS. 1 to 2 and the above discussion is equally applicable in the most instances.

The sleeve member 30, the actuator 40 and the oscillator 50 in the above embodiment are now modified or removed. Instead there is a sleeve member 30a in which the upper portion remains unchanged but a large diameter lower portion 39 is reformed, a shoulder 391 is defined between the upper portion and the lower portion and a pair of first and second arcuate projections 392 and 393 of sloped ends are formed spaced apart on opposite circumference of the shoulder 391 and follow the arc of the shoulder 391. The first projection 392 is positioned inner than that of the second projection 393 so that they are positionally alternate relative to the arc surface of the shoulder 391. A driven member 50a directly secured to the lower end of the axle rod 56 and rotatably disposed inside the lower portion 39 of the sleeve member 30a. The driven member 50a has a cylinder body 51a, a protrusion 52a laterally extended from a periphery and a vertical slot 53a on a periphery opposite to the protrusion 52a. The recoil spring 57 sleeves onto the cylinder body 51a having one end secured into the vertical slot 53a and the other end to a inner wall of the lower portion 39 of the sleeve member 30a. A second actuator 40a has a flat circular body 41a, a rectangular central bore 42a sizeably equal to the configuration of the shaft 21 of the motor 20, a third arcuate projection 43a projected upward from the upper surface thereof and made in registry with the first projection 392 and a fourth arcuate projection 44a projected upward from a circumference thereof and made in registry with the second projection 393 of the sleeve member 30a. Both the third and fourth projections 43a and 44a have a slope at each end so that they can slide onto the first and second projections 392 and 393, respectively, during the rotation of the actuator 40a. The third projection 43a further has a conductor 45a perpendicular to one end and extended inward. The conductor 45a is made operationally in cooperation with the protrusion 52a of the driven member 50a.

The motor 20 is unchanged but the shaft 21 is exactly at the center of the motor 20 without eccentric arrangement and a seat 22 is added thereon.

When the second actuator 40a slides onto the shaft 21, a compression spring 23 biases between the actuator 40a and the seat 22 so that the actuator 40a is driven to rotate counterclockwise by the motor 20 and slides up and down on the shaft 21. When the sleeve member 30a is assembled, the second actuator 40a is at an upmost position inside the sleeve member 30a and the projections 392, 44a, 393 and 43a are to juxtaposed each other where the conductor 45a is laterally engageble with the protrusion 52a (as shown in FIG. 5A).

Figure 5C:
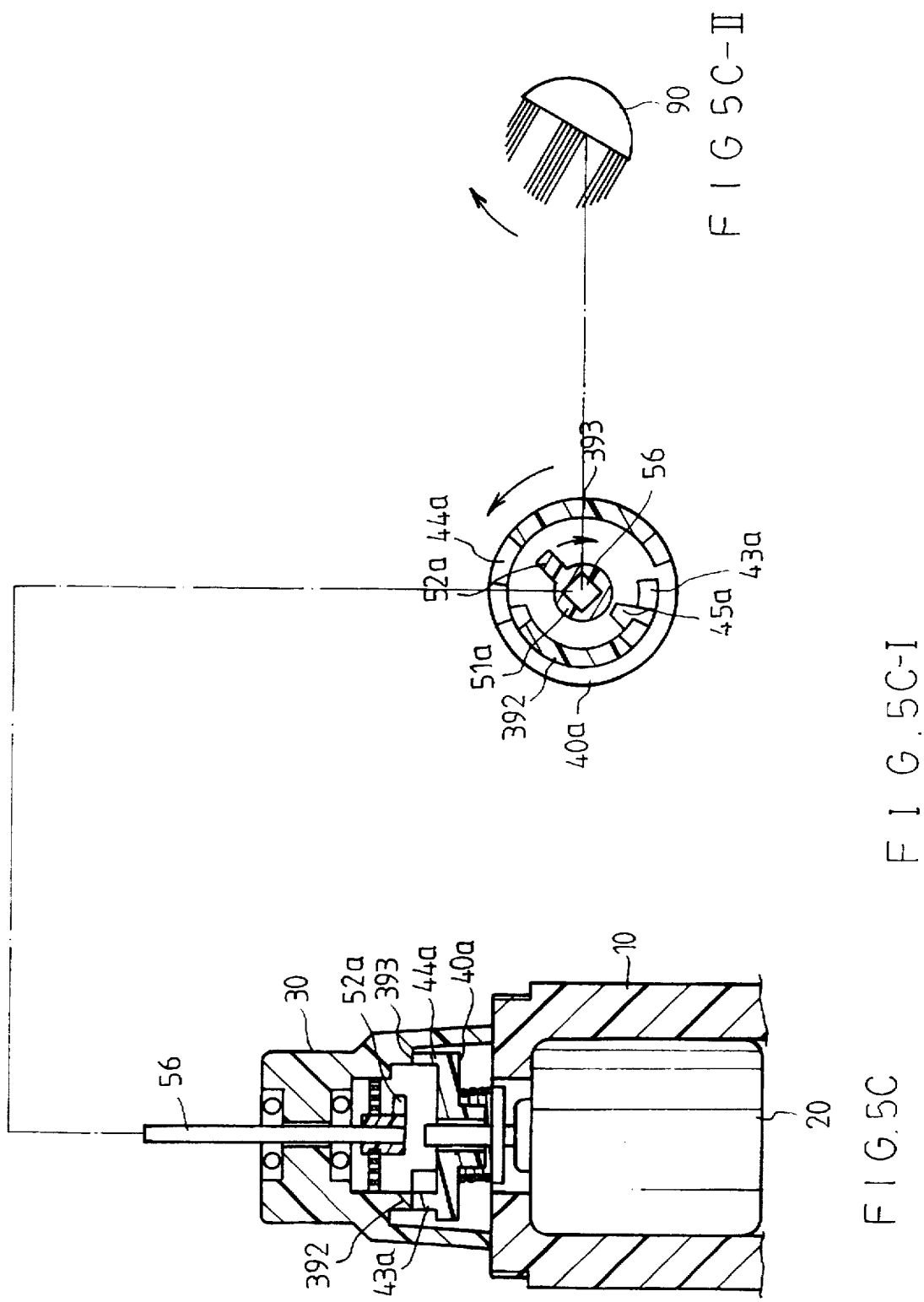

In operation, the protrusion 52a of the driven member 50a is pushed by the conductor 45a moving counterclockwise until the third and the fourth projections 43a and 44a reached the sloped ends of the first and second projections 392 and 393, respectively, and superposed thereupon so that the protrusion 52a is disengaged with the conductor 45a and returned back to normal position under the recoiling force of the spring 57 (as shown in FIGS. 5B and 5C). When the projections 43a, 392, 44a and 393 are disengaged with each other, the second actuator 40a slides upward under resilient force of the compression spring 23 and the conductor 45a engages with the protrusion 52a to push it to rotate again (as shown in FIG. 5D). As the second actuator 40a is driven to rotate continuously by the motor 20, the driven member 50a will be acted forward and backward repeatedly, as recited in the above embodiment, and the toothbrush 90 is indirectly driven to perform continuous oscillatory movement within a certain range of angle. Although there is no bumping occurred in this embodiment, the intermittent elastic vibrations are also provided because of the recoiling force of the spring 57.

Note that the specification relating to the above embodiments should be construed as exemplary rather than as limitative of the present invention, with many variations and modifications being readily attainable by a person of average skill in the art without departing from the spirit or scope thereof as defined by the appended claims and their legal equivalents.

I claim:

1. An electrically operated oscillatory toothbrush comprising:

- a tubular housing, said housing having a smaller diameter bottom at an upper end of the housing including a first axial hole with peripheral threads, an externally threaded neck at a lower end thereof, a first chamber and a larger diameter second chamber defining a shoulder thereinbetween;
- an electric motor axially secured in the first chamber of said housing and having a rectangular shaft eccentrically arranged on a top of the motor and exposed exterior of said housing;
- a battery axially disposed in the second chamber of said housing and secured by a cover;
- an actuator sleeved onto the rectangular shaft of said motor, said actuator having an annular body, a rectangular hole made in registry with the rectangular shaft and a push means laterally extending from an outer periphery of the annular body;
- an oscillator covering said actuator and positioned above an upper surface of the bottom of said housing, said oscillator having an annular body, an upper end, a first transverse recess formed through a peripheral wall, a smaller diameter member centrally formed above the upper end including a rectangular central bore for securing a rectangular axle rod, and a vertical slot in the peripheral wall for securing one end of a recoil spring therein, and a pawl means inserted into the first transverse recess and positionably engageable with the push means of said actuator;
- a sleeve member covering said oscillator and the other end of said recoil spring being connected to an inner wall of the sleeve member, said sleeve member having a hollow cylinder body defining a third chamber therein, an upper end including a second axial hole at a center thereof, a second transverse recess of predetermined length in a peripheral wall of the hollow cylinder body for sliding the pawl means therein, first and second circular cavities formed on opposite sides of the upper end for respectively receiving first and second bearings therein, said first and second bearings each having a rectangular central bore sizeably equal to the body of said rectangular axle rod;
- a chuck member axially inserted onto said axle rod and positioned against the first bearing, said chuck member having a cylinder body, a rectangular central bore made in registry with the body of said rectangular axle rod and a tapered upper end in which a plurality of vertical slots are formed spaced apart;
- a cap member having a hollow cylinder body defining a fourth chamber to receive said sleeve member therein, a tapered upper portion including a third axial hole therein for passing said chuck member therethrough and a threaded neck at an upper end, a recess in a peripheral wall of the tapered upper portion for securing a switch therein, and a flange extended outward from a lower rim of the cop member and having a diameter equal to that of the upper end of said housing so that said cap member covers said upper end and is fastened by means of a locking ring;
- a third bearing sleeved on the tapered upper end of said chuck member, said bearing having a tapered central bore made in registry with the upper end of said chuck member;
- a fastening means fastened on the threaded neck of said cap member with said third bearing enclosed therein, said fastening means having an annular body with peripheral threads on an internal wall and a fourth axial hole centrally formed therein;
- a toothbrush axially inserted into the upper end of said chuck member and fastened by said fastening means, said toothbrush having a bristle head, a shank, a connection rod and an annular groove formed around a periphery of the shank thereof;
- a waterproof means secured between the annular groove of said toothbrush and said fastening means, said waterproof means having a flexible conical body, a maximum diameter equal to the diameter of said fastening means and a minimum diameter equal to the diameter of the annular groove;
- a tubular cover on said toothbrush.

2. An electrically operated oscillatory toothbrush comprising:

- a tubular housing, said housing having a smaller diameter bottom at an upper end of the housing including a first axial hole with peripheral threads, an externally threaded neck at a lower end thereof, a first chamber and a larger diameter second chamber defining a shoulder thereinbetween;
- an electric motor axially secured in the first chamber of said housing and having a rectangular shaft including a seat means projected from the center thereof and exposed upward exterior of said housing;
- a battery axially disposed in the second chamber of said housing and secured by a cover;
- an actuator sleeved onto the rectangular shaft of said motor and biased by means of spring between an under side of the actuator and said seat means, said actuator having a flat circular body, a rectangular central bore sizeably equal to the rectangular shaft, a third arcuate projection projected upward from an upper surface of the actuator and positioned between the rectangular central bore and a periphery of the flat circular body and having a conductor means perpendicular to one end thereof and a slope at other end thereof, and a fourth arcuate projection projected upward from the upper surface of the actuator opposite to the third arcuate projection and positioned along the periphery of the flat circular body, the fourth arcuate projection being sloped at each end;
- a sleeve member covering said actuator on the top of said housing, said sleeve member having a hollow cylinder body defining a third chamber therein which includes a smaller diameter upper portion and a larger diameter lower portion defining a shoulder thereinbetween, the upper portion having a second axial hole at a center and a pair of circular cavities on opposite sides thereof of the upper portion for respectively securing first and second bearings therein, a first sloped arcuate projection projected outward from a circumference of the shoulder thereof made in registry with the third arcuate projection of said actuator and a second sloped arcuate projection projected outward from the shoulder positioned opposite to the first arcuate projection made in registry with the fourth arcuate projection of said actuator;

a driven member axially and rotatably secured into the third chamber of said sleeve member through the first and the second bearings, said driven member having a cylinder body, a rectangular recess at a center of an upper end of the cylinder body for securing a rectangular axial rod therein, a protrusion laterally extended from a periphery of the cylinder body and a vertical slot formed in an opposing periphery thereof for securing one end a recoil spring therein, said recoil spring an other end secured to an inner wall of the third chamber of said sleeve member;

a chuck member axially inserted onto said axle rod and positioned against the first bearing, said chuck member having a cylinder body, a rectangular central bore made in registry with the body of said rectangular axle rod and a tapered upper end in which a plurality of vertical slots are formed spaced apart;

a cap member having a hollow cylinder body defining a fourth chamber to receive said sleeve member therein, a tapered upper portion including a third axial hole therein for passing said chuck member therethrough and a threaded neck at an upper end, a recess in a peripheral wall of the tapered upper portion for securing a switch therein, and a flange extended outward from a lower rim of the cop member and having a diameter equal to that of the upper end of said housing so that said cap member covers said upper end and is fastened by means of a locking ring;

a third bearing sleeved on the tapered upper end of said chuck member, said bearing having a tapered central bore made in registry with the upper end of said chuck member;

a fastening means fastened on the threaded neck of said cap member with said third bearing enclosed therein, said fastening means having an annular body with peripheral threads on an internal wall and a fourth axial hole centrally formed therein;

a toothbrush axially inserted into the upper end of said chuck member and fastened by said fastening means, said toothbrush having a bristle head, a shank, a connection rod and an annular groove formed around a periphery of the shank thereof;

a waterproof means secured between the annular groove of said toothbrush and said fastening means, said waterproof means having a flexible conical body, a maximum diameter equal to the diameter of said fastening means and a minimum diameter equal to the diameter of the annular groove;

a tubular cover on said toothbrush.

* * * * *